United States Patent [19]

Beck et al.

[11] Patent Number: 4,713,052
[45] Date of Patent: Dec. 15, 1987

[54] APPARATUS FOR ASPIRATING SECRETED FLUIDS FROM A WOUND

[75] Inventors: Walter Beck, Obere Häslibachstr. 87, CH-8700 Küsnacht; Siegfried Berger, Wernau; Margrit Werner, Lion-Feuchtwanger Str. 69, 6500 Mainz-Hechtsheim, all of Fed. Rep. of Germany

[73] Assignees: Walter Beck; Margrit Werner, both of Fed. Rep. of Germany

[21] Appl. No.: 798,844

[22] Filed: Nov. 18, 1985

[30] Foreign Application Priority Data

Nov. 16, 1984 [DE] Fed. Rep. of Germany ....... 3441893

[51] Int. Cl.⁴ ............................................. A61M 31/00
[52] U.S. Cl. ...................................... 604/48; 604/118
[58] Field of Search ...................... 604/22, 27, 31, 35, 604/48, 118, 119; 128/DIG. 13; 73/861.42, 723, 724

[56] References Cited

U.S. PATENT DOCUMENTS 3,967,504  7/1976  Akeley ............................. 73/861.47
4,080,966  3/1978  McNally et al. ........... 128/DIG. 13
4,496,342  1/1985  Banko ................................... 604/22

*Primary Examiner*—John D. Yasko
*Assistant Examiner*—J. L. Kruter
*Attorney, Agent, or Firm*—Wigman & Cohen

[57] ABSTRACT

A method provided for aspirating secreted fluids from a wound by means of a drain connected to a negative pressure source with variable negative pressure, the negative pressure effective at the drain being adjusted in accordance with a selectable pressure/time diagram. Also disclosed is an apparatus for carrying out the aforementioned method consisting of a negative pressure measuring device and a regulator controlling the negative pressure source, which regulator has inputs for the actual value determined by the negative pressure measuring device and for the prescribed set point value of the negative pressure.

5 Claims, 4 Drawing Figures

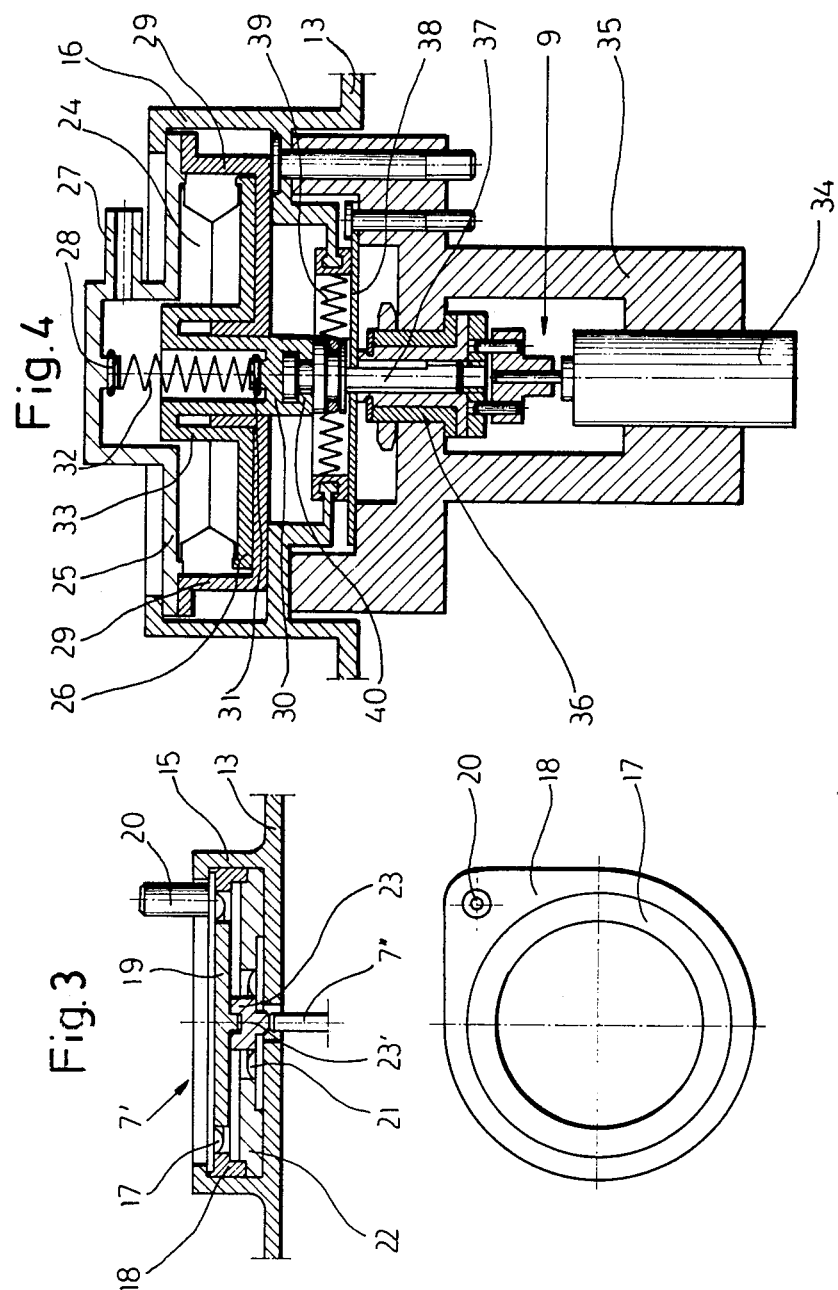

APPARATUS FOR ASPIRATING SECRETED FLUIDS FROM A WOUND

CROSS REFERENCE TO RELATED APPLICATION

This application is related to concurrently filed application entitled Method and Apparatus for Aspirating Secreted Fluids from a Wound, assigned U.S. application Ser. No. 798,845 commonly assigned.

BACKGROUND OF THE INVENTION

The invention relates to a method for aspirating secreted fluids from a wound by means of a drain connected to a negative pressure source having a variable negative pressure, and to an apparatus for performing this method.

In the postoperative aspiration of secreted fluids from a wound, the negative pressure is generally minimized according to the total aspirated quantity of secreted fluid, since the negative pressure source is a bottle or the like to which the drain is connected by means of a tube. It is also known to periodically increase and lower the suction effect. A pump is used for this purpose as the negative pressure source, which at predetermined time intervals is switched from a lower suction effect to a higher suction effect and vice versa. In addition, it has already been proposed to switch a pump of this type between a minimum and a maximum effect depending on the quantity of secreted fluid present. But none of these known methods leads to an optimal healing of the wound, which would require that the aspiration be adapted to the wound, particularly to the type of wound. An adaptation of this type is not possible with the known methods.

OBJECTS AND SUMMARY OF THE INVENTION

The object of the invention, therefore, is to provide an improved method for aspirating secreted fluids from a wound which makes possible an optimal adaptation of the aspiration to the wound. Other objects and advantages of the present invention will become apparent from the description which follows.

Since the negative pressure acting on the drain can be selected according to given requirements within the total time frame from the beginning to the end of the aspiration process, a sufficient range of adaptation is possible for any wound to facilitate the optimal healing process. In addition, the proper selection of the negative pressure as the drain is removed achieves a significant reduction in tissue damage in the wound.

The negative pressue can be set in various ways. For example, the changes necessary to maintain the pressure/time diagram can be made from time to time manually, in digital or analog form. Of course, the entire pressure/time diagram can also be entered, for example, in a memory or a data base. In one preferred embodiment, the pressure/time diagram is indicated as a pressure set point value and the actual pressure value can be measured and adjusted to the set point value. This has the advantage that the maintenance of the pressure/time diagram is not dependent on the attentiveness or reliability of the personnel, which is of particular importance in the area of postoperative treatment.

In contrast to an increase in the negative pressure, which can be effected by activating a pump, a decrease in the negative pressure in the use of a closed system, i.e., a system into which only the secreted fluids but not air can enter from the outside, is not a simple matter. Therefore, in a preferred form of the method according to the invention the negative pressure acting on the drain is lowered by reducing the volume in which the negative pressure prevails.

Another aspect of the present invention is to provide apparatus for carrying out the aforementioned method which permits the negative pressure acting on the drain to follow a freely selectable pressure/time diagram.

It would indeed also be possible from time to time for a person to read the prevailing negative pressure from the negative pressure measuring device and to correct it to the set point value after a comparison with the indicated pressure/time diagram. The use of a regulator, however, is advantageous as a rule, both with respect to the relatively high personnel costs and with respect to the elimination of possibilities for error traceable to human mistakes. This is true particularly since an embodiment of the apparatus according to the invention can be made so that all of the elements subjected to the negative pressure are disposable and thus a closed system can be realized at relatively low cost.

It is particularly advantageous according to the present invention to form the negative pressure source as a section of the tube leading from the drain to the collecting container, which can be subjected to the effect of a tube pump. The regulator hereby can adjust the rotational speed of the head of the tube pump acting on the tube section in the range between the rotational speed of 0 and the maximum rotational speed. Nevertheless, the attachment of the connection between the tube leading from the drain to the collection container and the pump head, and the detachment of this connection is so simple that the operation of the system by this means for the personnel is not impeded.

In order that the negative pressure measurement device result in the lowest possible expense, it is divided in a preferred embodiment into a sensor element and an evaluating element. The sensor element is advantageously formed as a disposable element comprising plastic and having two diaphragms of different surface sizes that act toward one another. In this manner, the relative movements of the two diaphragms can be translated in a simple manner into a pressure force that can be picked up from the outside, permitting significantly simpler coupling to the evaluating element that would be the case if a tensile force had to be picked up. Preferably, a holder for the sensor element is provided into which the sensor element need be placed or inserted in order to couple it with the evaluating element. The holder is placed in a housing that can also contain the evaluating element of the negative pressure measuring device as well as other components of the apparatus, for example, the head of the tube pump and its drive motor as well as the regulator. This also does not noticeably complicate the operation of the preferably closed system.

In order to be able to briefly decrease the prevailing negative pressure, the apparatus according to the present invention preferably includes a hollow element with a variable volume, the inside chamber of which communicates with that of the tube leading to the drain. With regard to the required sterility and its realizability as an element of a closed disposable system, this hollow element is preferably formed by a folding bellows, the two frontal walls of which can be adjusted relative to each other by means of a drive device in the longitudinal bellows direction. For the volumes usually required, a plastic folding bellows of this type can be manufactured at relatively low cost. One need only be sure that the coupling with its drive device is formed in such a manner that they can be engaged and disengaged without difficulty. For this purpose, it is effective to provide a holder, for example in the housing, that also contains the other components.

With the foregoing and other objects, advantages and features of the invention that will become apparent hereinafter, the nature of the invention may be more clearly understood by reference to the following detailed description of the invention, the appended claims and to the several views illustrated in the attached drawings.

BRIEF DESCRIPTION OF THE DRAWINGS

FIG. 3 is a longitudinal section through the sensor element of a negative pressure measuring device; and FIG. 4 is a longitudinal section through the hollow element having variable volume, and its drive device.

DETAILED DESCRIPTION OF A PREFERRED EMBODIMENT

Figure 1:
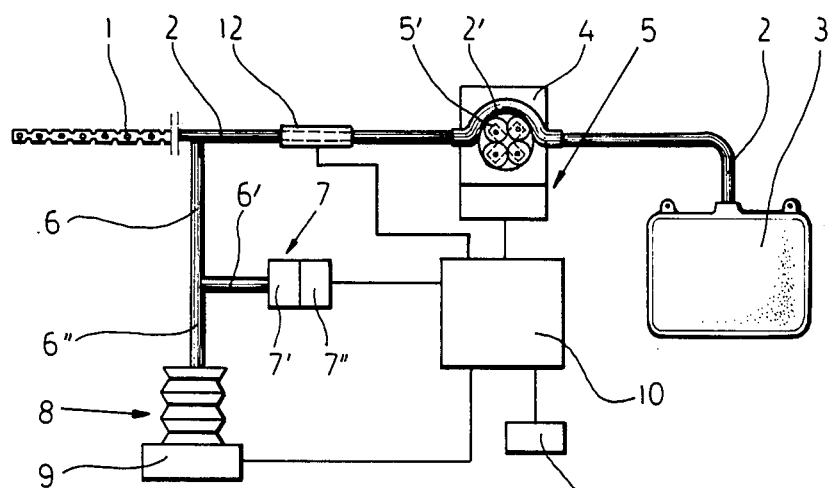
FIG. 1 is a schematic illustration of the exemplary embodiment.

As shown in FIG. 1, a drain 1 is connected with a collection container 3 by means of a tube 2, which collection container 3 receives the secreted fluids aspirated from the wound. The tube 2 has a section 2' which can be placed in a receptacle 4 into which there projects the rotatable head of a tube pump 5, which is formed in a known manner and is therefore not illustrated in detail. The head of the tube pump 5 is provided with rotatably mounted rollers 5', which, as long as they rest under pressure against the section 2' during the rotation, roll thereon. An electric motor with a regulatable rotational speed serves as the drive for the tube pump 5.

A second tube 6, which is branched, is connected with the tube 2. The first branch 6' leads to a sensor element 7' of a negative pressure measuring device 7, and the second branch 6" leads to a hollow element of variable volume, designated generally with 8, the inside of which therefore communicates with the inside chamber of the tube 2.

The hollow element 8 is connected with a drive device 9 by a detachable connection, by means of which drive device 9 the volume of the hollow element 8 can be set at different values. In the exemplary embodiment the maximum volume of the hollow element 8 is about 20 ccm. Of course, the volume can be selected larger or smaller according to given requirements.

The drain 1, the two tubes 2 and 6, the collection container 3, and sensor element 7' and the hollow element 8 form a closed system in a microbiological respect, i.e., during the entire period of use of these parts of the apparatus according to the invention, no causitive organisms can enter the interior of the system from the outside.

The rotational speed of the tube pump 5 is regulated in the range between 0 and the maximum rotational speed by a regulator 10, and this is done in such a manner that the actual value of the negative pressure in the second tube 6, which is identical to the actual value of the negative pressure effective at the drain 1, always agrees with the corresponding set point value prescribed by a pressure/time diagram. For this purpose the regulator receives electrical signals from an evaluating element 7" of the negative pressure measuring device, which is detachably connected with the sensor element 7', which electrical signals represent the actual value. Accordingly, the regulator 10 receives the set point value of the negative pressure from a set point value indicator 11. In the exemplary embodiment this set point value indicator is a memory from which the individual set point values can be read at the appropriate times. The set point value program, however, could of course also be constructed in a different manner, such as on a magnetic card capable of being inserted into a reading device in the set point value indicator.

A drive device 9 is also connected with the regulator 10 and is activated by the regulator in the sense of a volume reduction, when the pressure/time diagram prescribes a reduction in the negative pressure. If this diagram contains several negative pressure reduction steps, the regulator 10 must activate the drive device in the sense of a volume enlargement at the first negative pressure increase following a reduction of the negative pressure.

In the exemplary embodiment the tube 2 can be placed into a secreted fluid sensor 12 in the area between the section 2' and the drain 1. This sensor 12 is connected with an evaluating logic illustrated in FIG. 1 as part of the regulator 10, which evaluating logic is also connected with the output of the regulator 10 for the tube pump 5 and the evaluating element 7" of the negative pressure measuring device 7. The evaluating logic produces a signal if the tube pump 5 cannot increase the negative pressure in the tube 2 above a predetermined value, although it runs at maximum rotational speed, or if this tube pump 5 runs at a rotational speed lying above a predetermined limiting value and the secreted fluid sensor 12 does not report secreted fluid. In both cases, this is an indication of a leakage, for example, a wound that is not tightly closed.

Figure 2:
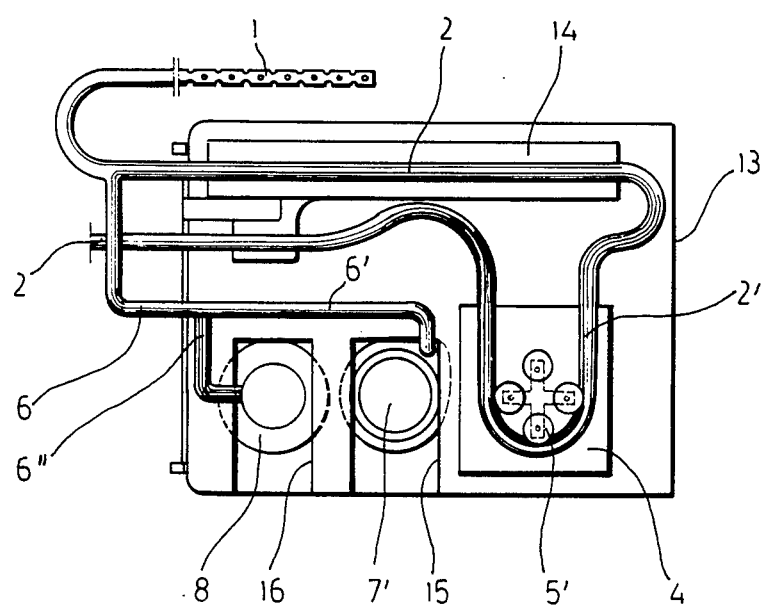
FIG. 2 is a top view of the housing containing different components.

The housing 13 illustrated in FIG. 2 contains the tube pump 5, the evaluating element 7" of the negative pressure measuring device 7, the drive device 9 for the hollow element 8, the regulator 10, the evaluating logic, the set point value indicator 11 and the secreted fluid sensor 12 as well as an energy supply element. The receptacle 4, into which the section 2' of the tube 2 is placed and into which the head of the tube pump 5 with the rollers 5' projects, is formed on one of the housing walls, which in the exemplary embodiment is the upper side of the housing. In addition, the upper side of the housing 13 forms a holder 14 for the secreted fluid sensor 12, so that the portion of the tube 2 leading from the drain 1 to the section 2' need only be placed into this holder 14 in order to be able to report secreted fluid. Finally, the upper side of the housing 13 is provided with receptacles 15 and 16 for the sensor element 7' of the negative pressure measurement device 7 and the hollow element 8, respectively.

As shown in FIG. 3, the sensor element 7', which consists solely of plastic, has a first diaphragm 17, the outer edge of which is rigidly connected with an annular element 18, or is formed in one piece therewith. An annular disk-shaped reinforcing plate 19 rests against the inner side of the central area of the first diaphragm 17, which reinforcing plate, however, can also be formed in one piece with the first diaphragm 17. In this case, the annular disk-like diaphragm element can be formed by a thin area between the reinforcing plate 19 and the annular element 18. A tube connection support 20 is formed on the annular element 18, the bore of which communicates with the inside of the sensor element 7'. A second diaphragm 21, the diameter of which is significantly smaller than that of the first diaphragm 17, lies parallel to and spaced from the first diaphragm 17. The outer edge of the second diaphragm 21 is held by an annular, rigid disk-like holder 22. The diaphragm 21 can also be formed in one piece with this holder 22, which is rigidly and sealingly connected with the annular element 18. A cylindrical spacing element 23 abuts the inside of the central area of the diaphragm 21, which spacing element 23 includes a central blind bore opening toward the reinforcing plate 19 in which there engages a centrally arranged pin of the reinforcing plate 19. In addition, the spacing element 23, which is sealingly connected with the second diaphragm 21, has a ram 23' that penetrates a central opening in the second diaphragm 21. Of course, the spacing element 23 could also be formed in one piece with the second diaphragm 21.

As a result of the severe differences in surface areas of the two diaphragms 17 and 21, an increasing evacuation of the sensor element 7' causes the ram 23' to move in a direction in which its projection beyond the outside of the holder 22 increases. The pressure force of the ram 23' and its longitudinal movement are translated by the evaluating element 7'', which has a measuring pin abutting the ram 23', into an electrical signal representing the level of the negative pressure.

In order to couple the sensor element 7' with the evaluating element 7'', the sensor element 7' need only be inserted into the associated receptacle 15 in the housing 13, which forms a contact surface for the outside of the holder 22 and overlaps the annular element 18. Similarly, at the completion of the aspiration, the sensor element 7' need only be removed from the receptacle 15.

In principle, the receptacle 16, into which the hollow element 8 is inserted in order to couple it with its drive device 9, is formed identically.

As shown in FIG. 4, the hollow element 8 has a folding bellows 24 consisting of plastic or rubber, which folding bellows 24 is sealed closed by an upper closure element 25 and a lower closure element 26. The upper closure element 25, as shown in FIG. 4, has the shape of a plate with an outwardly projecting hub that is open only toward the inside. A connection support 27 and a centrally arranged pin 28 are formed on the side and on the inside of the hub, respectively. The outer edge of the upper closure element 25 is securely and sealingly connected with an annular flange of a guide element 29 formed, like the closure elements, of plastic. This annular flange is connected to a cylindrical portion of the guide element 29, which concentrically surrounds the folding bellows 24 and is spaced therefrom. The cylindrical portion extends from an annular disc-like element toward the upper closure element 25 and said disc-like element lies parallel to said closure element 25. A central hub element, in which the lower closure element 26 is guided in a longitudinally movable manner by means of a hollow pin 30 that penetrates this hub element, extends in the same direction and is formed on the annular disc-like element. The outwardly directed end of the hollow pin 30 is closed.

A pin 31 directed toward the pin 28 is formed on the inside of the material section forming this closure. One or the other of the ends of a prebiased helical compression spring 32 is connected over both pins 28 and 31, which spring 32 loads the folding bellows 24 in the sense of an extension. The inner end of the hollow pin 30 is formed on a sleeve 33 which surrounds said pin and is spaced therefrom. This sleeve is guided so as to be longitudinally movable in the hub section of the upper closure element 25 and is formed in one piece with the rigid, annular disc-like element of the lower closure element 26, which can be moved in an axial direction and lies between the hub element and the hollow cylindrical element of the guide element 29.

The drive device 9 of the hollow element 8 is equipped with an electric motor 34, the rotational direction of which can be reversed, and which is arranged in a holder 35 in the housing 13 and is coaxially coupled with a sleeve 36 mounted in the holder 35 so as to be capable of rotation but incapable of axial movement. This sleeve 36 is provided with an internal threading, which engages with the threaded section of a coupling bolt 37, which is secured against rotation. To prevent this coupling bolt 37 from rotating, the threaded section of the coupling bolt 37 is provided with a longitudinal groove, in which a projection of a cover plate 38 engages. This projection is provided on the edge of a passage opening for the coupling bolt 37 in the cover plate 38.

Because the coupling bolt 37 can only perform a longitudinal movement and no rotation, the necessary sealing of the holder 35 toward the receptacle 16 presents no problems. As shown in FIG. 4, a folding bellows 39 of rubber is provided for this sealing, which folding bellows 39 has a central opening for the passage of the coupling bolt 37. This central opening is formed by a sealing ring which engages in an annular groove in the coupling bolt 37. The outside edge of the folding bellows 39 has the shape of a surrounding annular roll with an outwardly open annular groove. Annular roll of the receptacle 16 engages in this annular groove.

The end section of the coupling bolt 37 to be coupled with the hollow pin 30 is provided with an annular groove, in which two diametrically oppositely arranged claws 40 engage, which claws 40 are directed toward each other and project out from the frontal side of the hollow pin 30. When the hollow element 8 moves into the receptacle 16 laterally to the longitudinal direction of the hollow pin 30, the two claws 40 move into the associated annular groove in the coupling bolt 7. The coupling therefore occurs automatically when the hollow element 8 is placed in the receptacle 16, just as the uncoupling occurs during its removal from the receptacle 16.

Although only preferred embodiments, are specifically illustrated and described herein, it will be appreciated that many modifications and variations of the present invention are possible in light of the above teachings and within the purview of the appended claims without departing from the spirit and intended scope of the invention.

What we claim is:
1. Apparatus for aspirating secreted fluids from a wound comprising a controllable negative pressure source to which a drain is connected by means of a tube, a container for collecting the aspirated secreted fluid, a negative pressure measuring device and a regulator which controls the negative pressure source with inputs for the actual value determined by the negative pressure measuring device and for the prescribed set point values of the negative pressure, further including a hollow element having a variable inside volume, the inner chamber of which communicates with that of the tube leading to the drain, wherein the lateral boundary wall of the hollow element is formed by a folding bellows, drive means for adjusting the closure elements bounding the folding bellows at both sides relative to each other in the longitudinal direction of the bellows.

2. Apparatus for aspirating secreted fluids from a wound comprising a controllable negative pressure source to which a drain is connected by means of a tube, a container for collecting the aspirated secreted fluid, a negative pressure measuring device and a regulator which controls the negative pressure source with inputs for the actual value determined by the negative pressure measuring device and for the prescribed set point values of the negative pressure;

wherein the sensor element of the negative pressure measuring device is a plastic disposable element having two diaphragms of different surface areas that act in conjunction with each other;

wherein said diaphragms are two annular disc-like diaphragms and said sensor element further comprises holders formed in one piece therewith which form the two frontal surfaces of a can-like hollow element and a rigid central area; and wherein, the outer side of the rigid central area, which is surrounded by the annular disc-like diaphragm with the smaller diameter, includes a contact surface for a measurement converter, and the inner side thereof is supported by a spacing element on the rigid central area of the other diaphragm of larger diameter.

3. The apparatus according to claim 2 or 1 wherein the negative pressure source is formed by a section of the tube leading from the drain to the collection container and by a tube pump acting on this section.

4. The apparatus according to claim 1, wherein said closure elements bounding the frontal sides of the folding bellows and the folding bellows itself are parts of a disposable unit which can be placed in a holder in the housing, said housing containing the drive device and said disposable unit being coupled with the drive device by means of a coupling which engages as the unit is placed in the holder and disengages as it is removed.

5. The apparatus according to claim 3, further including a housing containing the tube pump, said housing includes holders for the tube section subjected to the effect of the tube pump and for the sensor element of the negative pressure measuring device.

* * * * *